United States Patent
Romero-Ortega et al.

(10) Patent No.: US 9,950,099 B2
(45) Date of Patent: Apr. 24, 2018

(54) DEVICES AND METHODS FOR THE PREVENTION AND TREATMENT OF NEUROMAS

(71) Applicant: BOARD OF REGENTS, THE UNIVERSITY OF TEXAS SYSTEM, Austin, TX (US)

(72) Inventors: Mario I. Romero-Ortega, Coppell, TX (US); Rafael Granja-Vasquez, Arlington, TX (US)

(73) Assignee: Board of Regents, The University of Texas System, Austin, TX (US)

(*) Notice: Subject to any disclaimer, the term of this patent is extended or adjusted under 35 U.S.C. 154(b) by 104 days.

(21) Appl. No.: 14/768,826

(22) PCT Filed: Feb. 18, 2014

(86) PCT No.: PCT/US2014/016801
§ 371 (c)(1),
(2) Date: Aug. 19, 2015

(87) PCT Pub. No.: WO2014/130419
PCT Pub. Date: Aug. 28, 2014

(65) Prior Publication Data
US 2015/0374887 A1 Dec. 31, 2015

Related U.S. Application Data

(60) Provisional application No. 61/766,368, filed on Feb. 19, 2013.

(51) Int. Cl.
*A61L 31/16* (2006.01)
*A61L 27/38* (2006.01)
(Continued)

(52) U.S. Cl.
CPC .......... *A61L 31/16* (2013.01); *A61B 17/1128* (2013.01); *A61B 17/12* (2013.01);
(Continued)

(58) Field of Classification Search
CPC .................................. A61B 17/1128
See application file for complete search history.

(56) References Cited

U.S. PATENT DOCUMENTS

| 4,778,467 A | 10/1988 | Stensaas et al. |
| 2003/0049839 A1* | 3/2003 | Romero-Ortega ... C12N 5/0068 435/397 |

(Continued)

FOREIGN PATENT DOCUMENTS

| CN | 101579247 B | 2/2012 |
| NL | 1036784 | 10/2010 |
| WO | 2007140597 A1 | 12/2007 |

OTHER PUBLICATIONS

Notification of Transmittal of the International Search Report and Written Opinion for corresponding PCT Application No. PCT/US2014/016801, dated May 12, 2014, 14 pages.

(Continued)

*Primary Examiner* — Thomas J Sweet
*Assistant Examiner* — Daniel Bissing
(74) *Attorney, Agent, or Firm* — John P. Zimmer; Smith Moore Leatherwood LLP

(57) ABSTRACT

In one aspect, nerve growth inhibition devices are described herein. In some embodiments, a nerve growth inhibition device described herein comprises a tube having a proximal end and a distal end. A matrix material is disposed in the tube, and the matrix material comprises one or more microchannels. The proximal end of the tube comprises an opening operable to receive nerve tissue, the distal end of the tube is sealed, and the microchannels of the matrix material (Continued)

extend from the proximal end of the tube toward the distal end of the tube.

22 Claims, 5 Drawing Sheets

(51) Int. Cl.
*A61B 17/11* (2006.01)
*A61B 17/12* (2006.01)
*A61L 31/04* (2006.01)
*A61B 17/00* (2006.01)

(52) U.S. Cl.
CPC ......... *A61L 27/3878* (2013.01); *A61L 31/041* (2013.01); *A61B 2017/00893* (2013.01); *A61L 2300/432* (2013.01)

(56) References Cited

U.S. PATENT DOCUMENTS

2008/0208300 A1* 8/2008 Pasch ................ A61B 17/1128 607/116
2008/0300691 A1* 12/2008 Romero-Ortega . A61B 17/1128 623/23.72
2011/0021943 A1* 1/2011 Lacour ................ A61N 1/0551 600/546

OTHER PUBLICATIONS

J. -U. Meyer et al., "Perforated silicon dices with integrated nerve guidance channels for interfacing peripheral nerves", Proceedings of the Workshop on Micro Electrical Mechanical Systems (MEMS), Workshop 8, Jan. 29, 1995, pp. 358-361.
Ivan R Minev et al. "High sensitivity recording of afferent nerve activity using ultra-compliant microchannel electrodes: an acute in vivo validation" (2012) J. Neural Eng. 9 026005.
Lacour et al. "Polyimide micro-channel arrays for peripheral nerve regenerative implants" Sensors and Actuators A 147 (2008) 456-463.
Navarro et al. "A Critical Review of Interfaces with the Peripheral Nervous System for the Control of Neuroprostheses and Hybrid Bionic Systems." Journal of the Peripheral Nervous System 10:229-258 (2005).

* cited by examiner

DEVICES AND METHODS FOR THE PREVENTION AND TREATMENT OF NEUROMAS

CROSS REFERENCE TO RELATED APPLICATION

This application is a U.S. national stage application under 35 U.S.C. § 371 of International Application No. PCT/US2014/016801, filed Feb. 18, 2014, which claims priority pursuant to 35 U.S.C. § 119(e) to U.S. Provisional Patent Application Ser. No. 61/766,368, filed on Feb. 19, 2013, each of which is hereby incorporated by reference in its entirety.

FIELD

This invention relates to devices and methods for the prevention and treatment of neuromas and, in particular, to devices and methods that inhibit erratic nerve growth.

BACKGROUND

The number of amputees in the world has risen significantly in recent years, with war injuries and dysvascular diseases such as diabetes accounting for approximately 90% of all amputee cases. There are currently about 1.7 million amputees living in the United States alone, and approximately 135,000 new amputee patients are discharged annually from hospitals. Further, it has been estimated that there will be a 20% increase in the number of new amputee cases per year by 2050.

Unfortunately, due to persistent pain in limb remnants, about 25% of amputees are not able to commence rehabilitation, much less resume ordinary daily activities. The cause of such pain can be a neuroma. One recent study reported that 78% of amputees experienced mild to severe pain as a consequence of neuroma formation over the 25-year study period, of which 63% described the pain as constant aching pain. The pain is also frequently described as sharp, shooting, or electrical-like phantom sensations that persist for years after surgical amputation. In addition, patients experience tenderness to palpation of the skin overlying the neuroma, spontaneous burning pain, allodynia, and hyperalgesia.

Neuromas are benign tumors that arise from neural tissue and are composed of abnormally sprouting axons, Schwann cells, and connective tissue. Even though neuromas can appear following various types of injuries, some of the most common and challenging to treat are derived from amputation surgeries in which neural tissue is sectioned by retraction axotomy. The lack of organ-target acquisition by the resulting nerve stump results in a subsequent cascade of biological events that culminate in the formation of a neural nodule.

To treat patients with painful neuromas, doctors have relied on multiple treatment modalities. However, many existing treatment modalities have a high recurrence rate, address the problem only after it has established itself in the patient, and/or are not definitive. A high neuroma recurrence rate can lead to repeated surgical resections. Further, the prevention of neuroma formation by some prior methods has also proven unsatisfactory, sometimes requiring multiple procedures. Therefore, there exists a need for improved devices and methods for the prevention and treatment of neuromas.

SUMMARY

In one aspect, nerve growth inhibition devices are described herein which, in some embodiments, can provide one or more advantages compared to some prior devices. For example, in some embodiments, a device described herein can be used to prevent painful neuroma formation, including from the first surgery. For example, devices described herein, in some cases, can be used for post-amputation surgery in which it is known that patients will otherwise likely develop a neuroma. It is also possible to use devices described herein at the time of the initial surgery in new amputee cases as well as in those who have already presented with pain of the nerve stump. Devices described herein, in some embodiments, can treat and/or prevent neuromas by hindering neuroma formation in the peripheral nervous system. In some cases, a device described herein can effectively block the natural progression of abnormal nerve sprouting that would otherwise translate into the formation of a painful neuroma. Further, devices described herein, in some instances, can also provide analgesia. For example, in some embodiments, a device described herein can provide at least partial analgesia by physically protecting an injured nerve from surrounding tissue and/or direct pressure, such as continually moving surrounding muscle tissue. Additionally, in some cases, a device described herein can provide at least partial analgesia by protecting an injured nerve from environmental electromagnetic radiation such as radio frequency (RF) radiation.

A nerve growth inhibition device described herein, in some embodiments, comprises a tube having a proximal end and a distal end. A matrix material is disposed in the tube, and the matrix material comprises one or more microchannels or lumens. The proximal end of the tube comprises an opening operable to receive nerve tissue, the distal end of the tube is sealed, and the microchannels of the matrix material extend from the proximal end of the tube toward the distal end of the tube. Further, in some cases, the tube is sealed with a capping material disposed in the distal end of the tube. The capping material, in some instances, blocks or substantially blocks the distal end of the one or more microchannels.

In addition, in some embodiments, the matrix material of the device, alone or in combination with the capping material, exhibits a compositional gradient from the proximal end of the tube toward the distal end of the tube. In some cases, the compositional gradient of the matrix material and/or capping material provides a nerve growth region and a nerve growth inhibition region within the tube. The use of such a device, in some instances, can induce nerve axons to enter the tube and grow toward the distal end of the tube (within the nerve growth region), followed by inhibition or total cessation of nerve growth within the tube (once the nerves reach the nerve growth inhibition region), thereby sequestering the nerve endings within the tube and preventing neuroma formation. In some embodiments, a matrix material, alone or in combination with a capping material, has a binary chemical composition comprising a nerve growth region and a nerve growth inhibition region. Alternatively, in other cases, a matrix material has a chemical composition that varies continuously or in a step-wise manner as a function of distance from the proximal end of the tube.

Moreover, in some embodiments, a device described herein further comprises a fluid, such as a saline solution, disposed in one or more microchannels of the device. Additionally, in some instances, one or more microparticles are disposed in the fluid, the microparticles comprising one or more nerve growth inhibition factors. The use of such microparticles, in some cases, can permit the time-delayed release of nerve growth inhibition factors into the microchannels of a device described herein. Further, in some embodiments, the microchannels of a device described herein are free or substantially free of an extracellular matrix (ECM) material, such as collagen, disposed within the microchannels.

In addition, a device described herein, in some cases, further comprises an electromagnetic radiation (EMR) shielding layer substantially surrounding the exterior circumference of the tube of the device. Such a shielding layer can be formed from an electrically conductive metal. A device described herein can also further comprise an encapsulation layer substantially surrounding the exterior of the EMR shielding layer. Such an encapsulation layer can be formed from an insulating material.

In another aspect, methods of treating and/or preventing a neuroma are described herein. In some cases, treating and/or preventing a neuroma comprises inhibiting nerve growth and/or providing analgesia in a biological compartment. In some embodiments, such a method described herein comprises disposing a device described herein in a biological compartment comprising nerve tissue. In some cases, the biological compartment comprises a stump of a severed or transected nerve. Further, in some embodiments, the device is disposed over the nerve stump.

These and other embodiments are described in more detail in the detailed description which follows.

DETAILED DESCRIPTION

Figure 1:
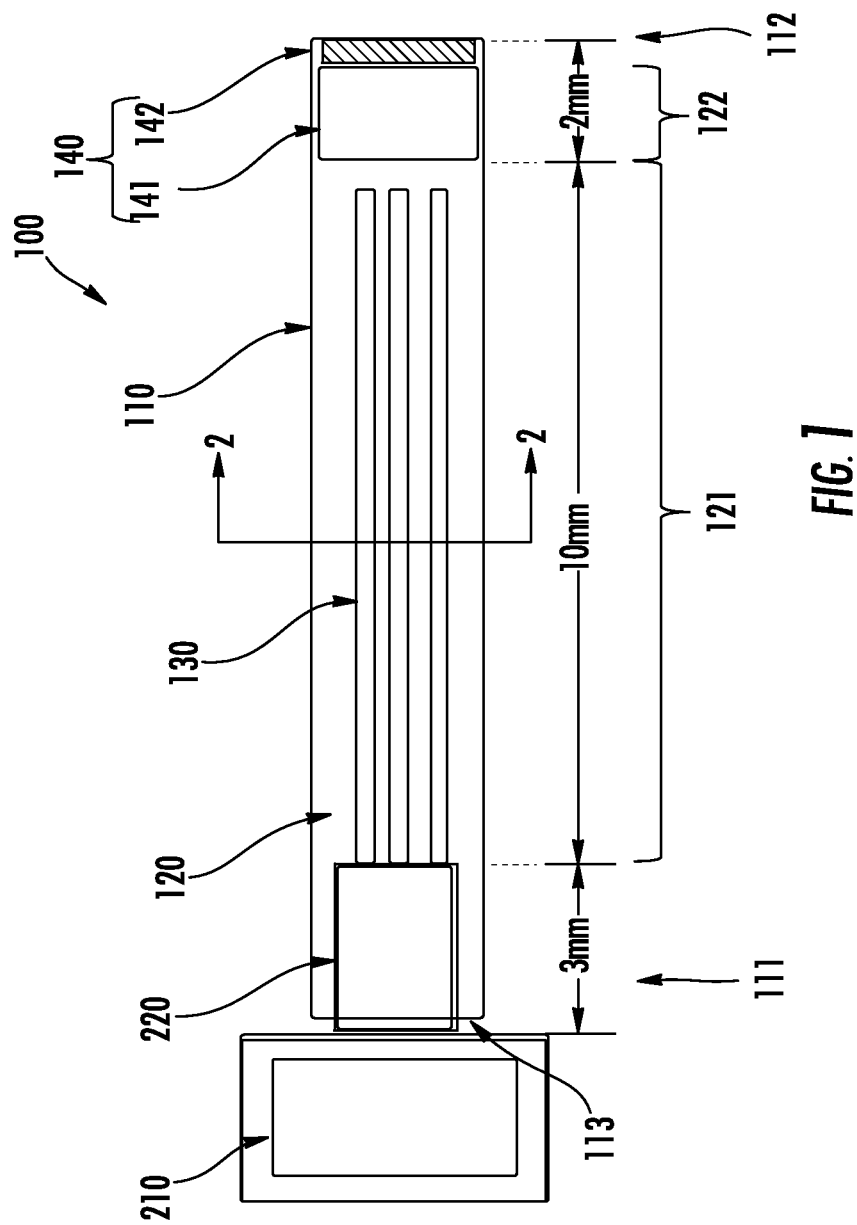
FIG. 1 illustrates a sectional, side view of a device according to one embodiment described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Nerve Growth Inhibition Devices

In one aspect, nerve growth inhibition devices are described herein. In some embodiments, a nerve growth inhibition device comprises a tube having a proximal end and a distal end; and a matrix material disposed in the tube and comprising or defining one or more microchannels, wherein the proximal end of the tube comprises an opening operable to receive nerve tissue, the distal end of the tube is sealed, and the microchannels of the matrix material extend from the proximal end of the tube toward the distal end of the tube. In addition, in some cases, a device described herein further comprises a fluid, such as a saline solution, disposed in one or more microchannels of the device. Additionally, in some instances, one or more microparticles are disposed in the fluid, the microparticles comprising one or more nerve growth inhibition factors. Moreover, in some embodiments, a device described herein further comprises an electromagnetic radiation (EMR) shielding layer substantially surrounding the exterior circumference of the tube. A device described herein can also comprise an encapsulation layer substantially surrounding the exterior circumference of the EMR shielding layer.

Turning now to specific components of devices, devices described herein comprise a tube having a proximal end and a distal end, wherein the proximal end of the tube comprises an opening operable to receive nerve tissue and the distal end of the tube is sealed. The tube and the opening of the tube can have any size, shape, and structure not inconsistent with the objectives of the present invention. In some embodiments, for instance, the tube has a substantially cylindrical shape. Further, in some cases, a tube described herein has an inner diameter between about 100 μm and about 50 mm, between about 1 mm and about 10 mm, or between about 1 mm and about 5 mm. In some cases, the tube has a diameter greater than about 50 mm or less than about 100 μm. The opening of a tube described herein, in some embodiments, can have the same inner diameter as the tube. Alternatively, in other instances, the opening can have a smaller size than the inner diameter of the tube. Further, in some cases, a tube described herein has a length between about 1 mm and about 200 mm, between about 5 mm and about 100 mm, between about 10 mm and about 30 mm, or between about 50 mm and about 150 mm.

Additionally, a tube described herein can comprise or be formed from any material not inconsistent with the objectives of the present invention. In some embodiments, for instance, the tube is formed from a polymeric material such as a polyurethane, a polyester, a polycarbonate, a polycaprolactone, a polylactic acid (PLA), a collagen, a polytetrafluoroethylene (PTFE), a polymethylmethacrylate (PMMA), an ethylene-vinylacetate copolymer (EVA), a polydimethylsiloxane (PDMS), a polyether polyurethane, a polyethyleneterephthalate (PET), a polysulfone (PS), a polyethyleneoxide (PEO) or polyethylene glycol (PEG), a polyethylene oxide-polypropylene oxide copolymer (PEO-PPO), a polyolefin such as polyethylene (PE) or polypropylene (PP), or a combination of one or more of the foregoing. In some instances, the tube comprises a segment of implantation or catheter tubing, such as Micro-Renathane implantation tubing. Other materials may also be used.

Further, in some cases, a tube described herein has a flat or curved surface on the sealed end of the tube, such that the tube is sealed by a wall formed from the same material that forms the remainder of the tube. The wall, in some cases, can be a flat or curved wall that is continuous with the remainder of the tube. In such an embodiment, the sealed end or wall of the tube can block or substantially block the distal end of the microchannels of the device, such that the microchannels of the device terminate at the sealed end of the tube. In other cases, the tube is sealed with a capping material disposed in the distal end of the tube. In this instance, the capping material can block or substantially block the distal end of the one or more microchannels. "Substantially" blocking the microchannels, for reference purposes herein, comprises blocking the microchannels sufficiently to prevent nerve tissue disposed in the microchannels from exiting the microchannels on the distal end. Therefore, the tube of a device described herein can be used to "cap" or otherwise isolate nerve endings and/or other nerve tissue.

Any capping material not inconsistent with the objectives of the present invention may be used. In some cases, for instance, a capping material comprises a gel, an adhesive, or a combination thereof. For example, in some instances, a capping material comprises agarose gel, a cyanoacrylate, or a combination thereof. Other gels and adhesives may also be used. Further, in some embodiments, a capping material comprises a plurality of capping layers. In some embodiments, for instance, a capping material comprises at least two layers or at least three layers. Moreover, the plurality of layers can comprise one or more gels, one or more adhesives, or a combination thereof. In some embodiments, a capping material comprises a first capping layer comprising an agarose gel and a second capping layer comprising a cyanoacrylate. Other configurations are also possible.

A capping material or a capping layer of a capping material described herein can have any thickness not inconsistent with the objectives of the present invention. For example, in some cases, a capping material forms a wall having a thickness between about 1 µm and about 100 mm, between about 10 µm and about 10 mm, between about 10 µm and about 1 mm, between about 50 µm and about 10 mm, between about 100 µm and about 10 mm, or between about 100 µm and about 1 mm. Other thicknesses are also possible. Moreover, the thickness of a capping material or capping layer described herein, in some cases, can be selected based on the composition of the capping material or capping layer used and/or a desired ability of the capping material or capping layer to prevent nerve growth through the capping material or capping layer.

Devices described herein also comprise a matrix material disposed in the tube of the device, the matrix material comprising one microchannel or a plurality of microchannels. The matrix material of a device described herein can comprise any number of microchannels not inconsistent with the objectives of the present invention. In some cases, for example, a matrix material comprises between 1 and 10 microchannels or between 1 and 5 microchannels. In addition, the microchannels can have any size not inconsistent with the objectives of the present invention. In some embodiments, for instance, the microchannels have an average diameter between about 100 µm and about 2000 µm, between about 100 µm and about 1000 µm, or between about 300 µm and about 800 µm. In some cases, the microchannels have an averge diameter of less than about 100 µm or greater than about 2000 µm. Further, the microchannels can have a length up to about 99%, up to about 95%, up to about 90%, or up to about 80% of the length of the tube of the device. Moreover, the size and/or number of microchannels in a device described herein, in some cases, can be selected based on the size of a nerve to be treated by the device, wherein a larger nerve may require a larger number and/or a larger size of microchannels for effective treatment. For example, in some cases, a device for the treatment of a nerve having a diameter of about 1.5 mm may comprise three microchannels having a diameter of about 600 µm each.

In addition, the matrix material of a device described herein can comprise or be formed from any material not inconsistent with the objectives of the present invention. In some cases, for instance, a matrix material comprises or is formed from a polymeric material. In some embodiments, a matrix material comprises or is formed from a hydrogel, such as, for example, a biodegradable hydrogel. A "biodegradable" material, for reference purposes herein, comprises a material that can decompose within a biological environment, and may provide a non-toxic decomposition product. In some embodiments, a biodegradable material described herein comprises one or more ester bonds. A matrix material described herein can also comprise or be formed from a non-biodegradable material, including a non-biodegradable polymeric material. In some instances, a matrix material described herein comprises an agarose gel. Any agarose gel not inconsistent with the objectives of the present invention may be used. In some cases, for example, a matrix material comprises an agarose gel comprising at least about 3 weight percent agarose, at least about 4 weight percent agarose, or at least about 5 weight percent agarose, based on the total weight of the agarose gel. In some embodiments, a matrix material comprises an agarose gel comprising between about 3 weight percent and about 10 weight percent agarose, between about 3 weight percent and about 8 weight percent agarose, or between about 3 weight percent and about 4 weight percent agarose, based on the total weight of the agarose gel. In other cases, a matrix material comprises an agarose gel comprising less than about 3 weight percent or less than about 2 weight percent agarose, based on the total weight of the agarose gel. In some instances, a matrix material comprises an agarose gel comprising between about 1 weight percent and about 2.5 weight percent agarose, based on the total weight of the agarose gel. Additional non-limiting examples of matrix materials suitable for use in some embodiments of devices described herein include polylactic-co-glycolic acid (PLGA), polylactic acid (PLA), polycaprolactone, polyurethane, polyester, polycarbonate, collagen, polytetrafluoroethylene (PTFE), polymethylmethacrylate (PMMA), an ethylene-vinylacetate copolymer (EVA), a polydimethylsiloxane (PDMS), polyether-polyurethane, a polyethyleneterephthalate (PET), a polysulfone (PS), a polyethyleneoxide (PEO) or polyethylene glycol (PEG), a polyethylene oxide-polypropylene oxide copolymer (PEO-PPO), a polyolefin such as polyethylene (PE) or polypropylene (PP), or a combination of one or more of the foregoing. Other matrix materials can also be used, alone or in combination.

Moreover, in some embodiments, the matrix material of a device described herein exhibits a compositional gradient from the proximal end of the tube toward the distal end of the tube. In some cases, the compositional gradient of the matrix material provides a nerve growth region and a nerve growth inhibition region within the tube, wherein the chemical composition of the nerve growth region differs from the chemical composition of the nerve growth inhibition region. A "nerve growth region" for reference purposes herein, comprises a spatial region in which nerve growth is promoted or at least not inhibited. A "nerve growth inhibition region," for reference purposes herein, comprises a spatial region in which nerve growth is inhibited. The promotion or inhibition of nerve growth in a nerve growth or nerve growth inhibition region described herein, in some instances, can be caused by the chemical composition of the region. Moreover, in some cases, the nerve growth region of a tube described herein is located closer to the proximal end of the tube than the nerve growth inhibition region is. Thus, in some embodiments, the use of a matrix material having a varying composition between the proximal end and the distal end of the tube of a device described herein can induce nerve axons to enter the tube and grow toward the distal end of the tube (within the nerve growth region), followed by inhibition or total cessation of nerve growth within the tube (once the nerves reach the nerve growth inhibition region), thereby sequestering the nerve endings within the tube and preventing neuroma formation.

Further, it is to be understood that the boundary between a nerve growth region and a nerve growth inhibition region of a device described herein can be a sharp boundary or a gradual boundary. For example, in some cases, a matrix material described herein, alone or in combination with a capping material described herein, has an essentially binary chemical composition, such that the compositional gradient forms sharply divided nerve growth and nerve growth inhibition regions within the tube. Alternatively, in other embodiments, the compositional gradient of the matrix material comprises a regularly changing gradient or a gradient having the form of a step function, wherein the chemical composition of the matrix material varies continuously or in a step-wise manner, respectively, as a function of distance from the proximal end of the tube.

For example, in some cases, a compositional gradient of a matrix material is provided by varying the weight percent of agarose in an agarose gel matrix material, where the weight percent of agarose is varied as a function of the distance from the proximal end of the tube. In some such embodiments, the weight percent of agarose increases as a function of distance from the proximal end of the tube. Moreover, the boundary between the nerve growth region and the nerve growth inhibition region of the matrix material in such an embodiment can be formed by the transition from a weight percent of agarose below about 3 weight percent or below about 2 weight percent (the nerve growth region) to a weight percent of agarose above about 3 weight percent or above about 2.5 weight percent (the nerve growth inhibition region). Other configurations of a compositionally graded matrix material are also possible.

Devices described herein, in some embodiments, further comprise a fluid disposed in one or more microchannels of the device. Any fluid not inconsistent with the objectives of the present invention may be used. In some cases, the fluid comprises a saline solution such as a sterile solution of sodium chloride in water. Non-limiting examples of saline solutions suitable for use in some embodiments described herein include normal saline (about 0.90% w/v NaCl) and hypertonic saline (about 3-7% w/v NaCl). Other saline solutions may also be used.

In addition, in some cases, one or more microparticles are disposed in the fluid of a device described herein. Moreover, the microparticles can comprise one or more nerve growth inhibition factors disposed within the interior and/or on the exterior surface of the microparticles. Any nerve growth inhibition factor not inconsistent with the objectives of the present invention may be used. In some embodiments, for example, a nerve growth inhibition factor comprises an axon regeneration inhibitor (ARI). Non-limiting examples of ARIs suitable for use in some embodiments described herein include chondroitin sulphate proteoglycans (CSPGs), myelin-associated glycoprotein (MAG), reticulon-4 (also known as Neurite outgrowth inhibitor or Nogo), and oligodendrocyte-myelin glycoprotein (OMgp). A nerve growth inhibition factor can be present in a microparticle described herein in any amount not inconsistent with the objectives of the present invention. In some embodiments, for instance, a nerve growth inhibition factor is present in a microparticle in an amount between about 0.0001 and about 1 weight percent, based on the total weight of the microparticle.

Further, a microparticle can have any size and shape and be formed from any material not inconsistent with the objectives of the present invention. In some embodiments, for example, a microparticle is a spherical or substantially spherical microparticle having a diameter between about 10 µm and about 1000 µm or between about 50 µm and about 500 µm. Microparticles having other sizes and shapes may also be used. In addition, in some cases, a microparticle is formed from a polymeric material, including any polymeric material described hereinabove for a tube or matrix material. Alternatively, in other instances, a microparticle is formed from an inorganic material such as silicon dioxide and/or titanium dioxide. Other materials may also be used.

The use of microparticles described herein, in some embodiments, can permit the time-delayed release of nerve growth inhibition factors into the microchannels of a device described herein. In this manner, a device described herein can facilitate nerve growth into and within the device at early time points following implantation of the device for the prevention and/or treatment of a neuroma, but inhibit or completely stop nerve growth within the device at later time points. Thus, in some embodiments comprising microparticles described herein, the matrix material of the device may or may not exhibit a compositional gradient described herein.

Additionally, in some cases, the microchannels of a device described herein are free or substantially free of an extracellular matrix material (ECM), such as collagen, disposed within the microchannels. A device that is "substantially" free of an ECM, for reference purposes herein, comprises a device that includes less than about 10 weight percent, less than about 5 weight percent, less than about 3 weight percent, less than about 1 weight percent, less than about 0.5 weight percent, or less than about 0.1 weight percent ECM disposed in the microchannels, based on the total weight of the contents of the microchannels.

Devices described herein, in some embodiments, further comprise an electromagnetic radiation (EMR) shielding layer. The EMR shielding layer can surround or substantially surrounding the exterior circumference of the tube of the device. For example, in some cases, the shielding layer surrounds at least about 70%, at least about 80%, at least about 90%, at least about 95%, or at least about 99% of the circumferential surface area of exterior of the tube. Moreover, in some embodiments, the shielding layer is disposed directly on the exterior surface of the tube. In other cases, one or more additional layers such as one or more adhesive layers are disposed between the tube and the shielding layer.

Further, the shielding layer of a device described herein, in some embodiments, can absorb and/or reflect incident EMR that would otherwise impinge on nerve tissue disposed within the device. In some cases, the shielding layer absorbs and/or reflects at least about 60%, at least about 70%, at least about 80%, at least about 90%, at least about 95%, or at least about 99% of incident radiation having a radio frequency (RF), such as a frequency between about 3 kHz and about 300 GHz, between about 3 kHz and about 30 kHz, between about 30 kHz and about 300 kHz, between about 300 kHz and about 3 MHz, between about 3 MHz and about 30 MHz, between about 30 MHz and about 300 MHz, between about 300 MHz and about 3 GHz, or between about 300 MHz and about 1000 MHz. In other instances, the shielding layer absorbs and/or reflects between about 60% and about 100%, between about 75% and about 99%, between about 80% and about 99%, between about 80% and about 95%, between about 85% and about 99%, or between about 90% and about 99.9% of incident EMR having a frequency described hereinabove.

The shielding layer of a device described herein can comprise or be formed from any material not inconsistent with the objectives of the present invention. For example, in some cases, a shielding layer comprises or is formed from an electrically conductive metal, including an elemental metal, metal alloy, or combination of metals. Any electrically conductive metal not inconsistent with the objectives of the present invention may be used. In some instances, a shielding layer comprises or is formed from one or more of cobalt, silver, copper, gold, aluminum, molybdenum, zinc, lithium, tungsten, brass, carbon, nickel, iron, palladium, platinum, tin, bronze, carbon steel, lead, titanium, and stainless steel. In other embodiments, a shielding layer comprises or is formed from an electrically conductive polymeric material. Any electrically conductive polymeric material not inconsistent with the objectives of the present invention may be used. In some cases, for instance, an electrically conductive polymeric materials comprises or is formed from a polypyrrole (PPY), a polyaniline (PANI), a polythiophene (PT), a poly(3,4-ethylenedioxythiophene) (PEDOT), a poly(p-phenylene sulfide) (PPS), a polyacetylene (PAC), a poly(p-phenylene vinylene) (PPV), or a combination of two or more of the foregoing.

Additionally, a shielding layer of a device described herein can have any thickness not inconsistent with the objectives of the present invention. In some embodiments, for instance, a shielding layer has a thickness between about 500 nm and about 1 mm, between about 500 nm and about 500 µm, between about 1 µm and about 500 µm, between about 1 µm and about 100 µm, between about 10 µm and about 500 µm, between about 10 µm and about 100 µm, between about 100 µm and about 1 mm, or between about 100 µm and about 500 µm. In some cases, a shielding layer has a thickness of less than about 500 nm or more than about 1 mm. Moreover, the thickness of a shielding layer described herein, in some cases, can be selected based on a desired absorptivity and/or reflectivity of the shielding layer.

The use of an EMR shielding layer described herein, in some embodiments, can reduce the amount of pain registered by a nerve disposed in a device described herein. In particular, the use of an EMR shielding layer can reduce the amount of pain induced by incident or environmental EMR.

A device described herein, in some cases, further comprises an encapsulation layer substantially surrounding the exterior circumference of an EMR shielding layer. Such an encapsulation layer can be formed from any material and have any thickness not inconsistent with the objectives of the present invention. In some embodiments, for instance, an encapsulation layer is formed from an electrically insulating layer such as a rubber or plastic. Other materials may also be used. Further, in some cases, an encapsulation layer described herein has a thickness between about 10 µm and about 10 mm. Other thicknesses may also be used.

Various components of devices have been described herein. It is to be understood that a device according to the present invention can comprise any combination of components and features not inconsistent with the objectives of the present invention. For example, in some cases, a device described herein comprises any tube described herein in combination with any matrix material described herein and any EMR shielding layer described herein.

Further, a device described herein can be made in any manner not inconsistent with the objectives of the present invention. In some instances, for example, a casting and/or negative extrusion process is used to form a tube or matrix material comprising one or more microchannels or lumens. In other embodiments, a device described herein is formed by 3D printing.

II. Methods of Preventing and Treating Neuromas

In another aspect, methods of preventing and treating neuromas are described herein. In some cases, preventing and/or treating a neuroma comprises inhibiting nerve growth and/or providing analgesia. In some embodiments, such a method comprises disposing a device described herein in a biological compartment comprising nerve tissue. Any device described hereinabove in Section I may be used. Further, the biological compartment can comprise any biological compartment not inconsistent with the objectives of the present invention. In some instances, the biological compartment comprises, consists, or consists essentially of nerve tissue, including nerve endings. In some cases, the biological compartment comprises a stump of a severed nerve, and the device is disposed on, over, or near the nerve stump. Additionally, in some cases, disposing a device described herein in a biological compartment described herein comprises surgically placing the device in the desired location.

Some embodiments described herein are further illustrated in the following non-limiting examples.

EXAMPLE 1

Device for Inhibiting Nerve Growth

A device for inhibiting nerve growth according to one embodiment described herein was prepared as follows. Specifically, a transparent multi-luminal (or multi-channel) matrix (TMM) casting device was used. Such a device is described in United States Patent Application Publication 2008/0300691, which is hereby incorporated by reference in its entirety. The TMM casting device consists of a square plastic open frame that accommodates an external polyurethane (or similar material) catheter tube with holes at opposite ends through which metal rods can be inserted. To form a device, the precursor of a desired matrix material described herein (such as an agarose gel) was added over the metal rods (such as titanium rods) disposed in the tube, followed by polymerization of the precursor to provide the matrix material. In this manner, the metal rods were effectively embedded in the matrix material. The metal rods were then removed from the frame to provide a matrix material comprising microchannels corresponding to the areas vacated by the metal rods. This matrix material could then be disposed within a tube described herein, including a tube sealed at the distal end.

Alternatively, a tube open on both ends could be disposed in the TMM frame prior to placement of the metal rods and the matrix material precursor within the tube. The fabrication procedure could then be completed as described above. It was also possible to provide a saline solution within the microchannels by disposing the saline solution in a loading well of the TMM prior to removal of the metal rods. The loading well was disposed such that the contents of the loading well were proximate the metal rods. Rapid removal of the metal rods resulted in a negative pressure within the microchannels, which was able to "pull" or "suck" the saline solution into the microchannels. Next, a separately formed capping material was prepared and disposed in the distal end of the tube to seal the distal end. In some cases, the capping material was disposed in the distal end of the tube after the tube was disposed over and sutured to a severed nerve. In such cases, an adhesive capping material could be polymerized in situ with saline.

Figure 2:
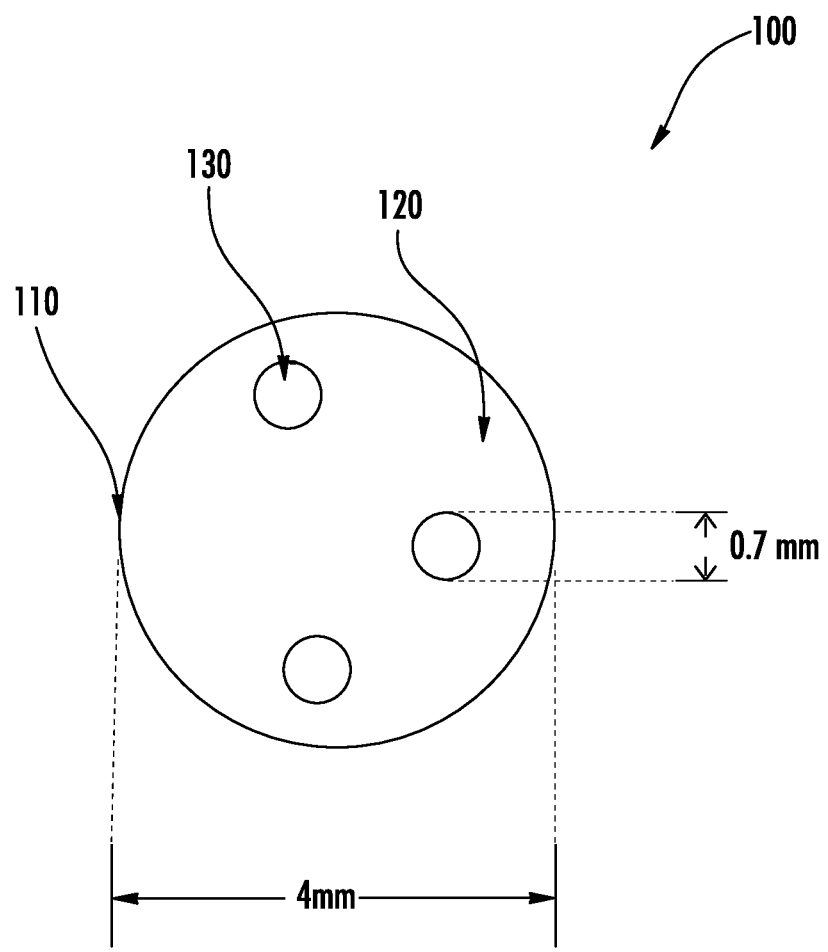
FIG. 2 illustrates a sectional view of the device of FIG. 1 taken along lines 2-2.

A device formed in this manner is depicted schematically in FIG. 1 and FIG. 2. FIG. 1 illustrates a sectional view of the device from the side. FIG. 2 illustrates a sectional view of the device taken along lines 2-2. As illustrated in FIGS. 1 and 2, the nerve growth inhibition device (100) comprises a polyurethane tube (110) having a proximal end (111) and a distal end (112). A matrix material (120) is disposed in the tube (110) and comprises a plurality of microchannels (130). The proximal end (111) of the tube (110) comprises an opening (113) operable to receive nerve tissue (not shown). The distal end (112) of the tube (110) is sealed, and the microchannels (130) of the matrix material (120) extend from the proximal end (111) toward the distal end (112) of the tube (110). In the embodiment of FIG. 1, the tube (110) is sealed with a capping material (140) disposed in the distal end (112) of the tube (110) and the capping material (140) blocks or substantially blocks the distal end (112) of the one or more microchannels (130). The capping material (140) comprises a first capping layer (141) comprising 3 wt. % agarose gel and a second capping layer (142) formed from a cyanoacrylate adhesive. The first capping layer (141) can also be considered to form a nerve growth inhibition region (122) within the device (100), in contrast to a nerve growth region (121) provided by the matrix material (120), which could be formed, for example, from 1.5 wt. % agaraose gel.

Further, as illustrated in FIG. 1, the device 100 is in fluid communication with a saline loading well (210) of a TMM casting device. The loading well (210) is in fluid communication with the microchannels through a tube insertion node (220).

EXAMPLE 2

Device for Inhibiting Nerve Growth

A device for inhibiting nerve growth according to one embodiment described herein is prepared as follows. The manufacturing process is carried out in a class 10,000 cleanroom environment. The process consists of semi-automated and manual steps. Semi-automated processes are performed using a manufacturing cell developed with a 3-axis gantry type positioning system having a payload capacity of 4 kg on the z-axis and a precision of 20 µm. The system includes the following process tools: a pick and place gripper; a dip coating gripper; and two precision dispensing syringes. The manufacturing cell contains multiple stations that include heating and cooling areas, a dip coating station, tools to create channels, and various fixtures to hold the device. Positioning is accomplished via precision touch sensors and encoders. Dispensing of the matrix material is performed by precision Engineered Fluid Dispensing (EFD) systems using heated syringes. The manufacturing cell is controlled by custom software written in Labview. Devices having different sizes of microchannels and/or tubes can be formed by altering the tooling of the manufacturing cell.

To manufacture a device comprising a tube formed from polyurethane, a sacrificial mandrill is used, the mandrill having a diameter that corresponds to the desired inner diameter of the polyurethane tube. The mandrill undergoes several dip coating and drying cycles in a polyurethane or polyurethane precursor solution. After the desired thickness of polyurethane is achieved on the mandrill, the dip-coated mandrill is removed to create the polyurethane tube. Next, an EMR shielding layer material is disposed on the outer surface of the polyurethane tube. The device is then vapor-sterilized. Finally, a TMM casting device similar to that described in Example 1 above is used to provide a matrix material comprising microchannels within the coated polyurethane tube. The TMM casting device can be pulled manually or by the robot pick and place gripper to form the microchannels.

Figure 3:
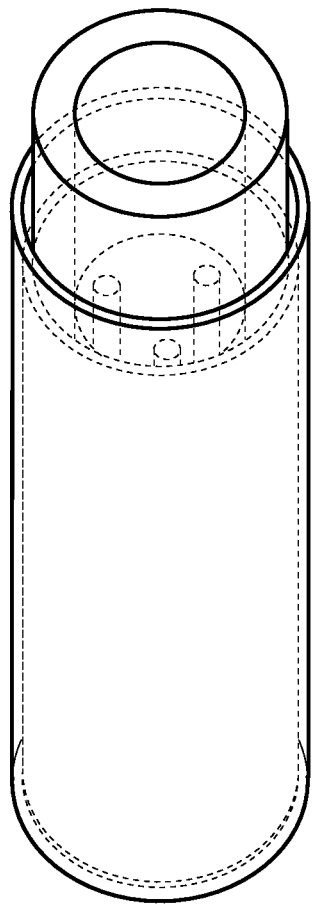
FIG. 3 illustrates a perspective view of a device according to one embodiment described herein.
Figure 4:
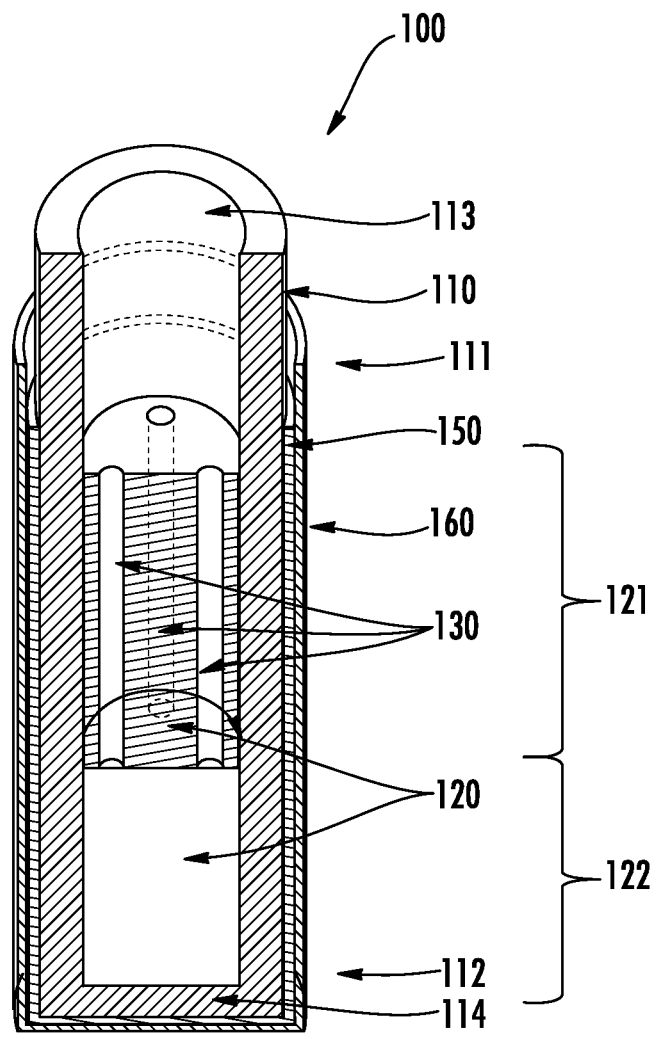
FIG. 4 illustrates a cutaway perspective view of the device of FIG. 3.

The resulting device is depicted schematically in FIG. 3 and FIG. 4. FIG. 3 illustrates a perspective view of the device. FIG. 4 illustrates a cutaway perspective view of the device. As illustrated in FIG. 4, the nerve growth inhibition device (100) comprises a tube (110) having a proximal end (111) and a distal end (112). A matrix material (120) comprising agarose gel is disposed in the tube (110) and comprises a plurality of microchannels (130). Further, the matrix material (120) has a binary chemical composition comprising a nerve growth region (121) and a nerve growth inhibition region (122). The nerve growth region (121) is provided by a matrix material composition comprising 1.5 wt. % agarose, and the nerve growth inhibition region (122) is provided by a matrix material composition comprising 3 wt. % agarose. The binary chemical composition of the matrix material (120) is provide by serially disposing the differing agarose gels within the tube (110). The proximal end (111) of the tube (110) comprises an opening (113) operable to receive nerve tissue (not shown). The distal end (112) of the tube (110) is sealed, and the microchannels (130) of the matrix material (120) extend from the proximal end (111) toward the distal end (112) of the tube (110). In the embodiment of FIG. 4, the tube (110) includes a sealed end comprising a wall (114) formed from the same material as the remainder of the tube (110). The wall (114) blocks or substantially blocks the distal end (112) of the one or more microchannels (130). An EMR shielding layer (150) is disposed on the exterior circumference of the tube (110). Further, an encapsulation layer (160) is disposed around the shielding layer (150). The EMR shielding layer (150) is formed by wrapping the EMR shielding material around the tube (110). The encapsulation layer (160) is formed by dip-coating with additional polyurethane.

EXAMPLE 3

Method of Inhibiting Nerve Growth

A method of inhibiting nerve growth according to one embodiment described herein was carried out as follows. Specifically, a device having the structure described in Example 1 was used to inhibit nerve growth or regeneration in rats (the "experimental" device). For comparison, a device similar to the device of Example 1 was used as a control (the "control" device). However, the tube of the control device was not sealed at the distal end. Instead, both ends of the tube of the control device included openings.

Both devices (control and experimental) were disposed over an acutely severed proximal nerve stump in living test animals and directed toward a distal nerve stump of the animals. Specifically, twenty adult Long Evans rats were used to test the regeneration inhibition method. Seven animals were treated with the control device and observed after 60 days (n=3) or 210 days (n=4). Thirteen animals were treated with the experimental device and observed after 60 days (n=5) or 210 days (n=8). Observation was carried out by photographing the implantation sites and by gross morphology of the harvested devices following the stated time period. The relative distance of tissue penetration through the length of the tubes of the devices was determined. The amount of tissue area per tube was also determined. For quantification purposes, recovered regenerated nerves were divided into proximal and distal segments and embedded in paraffin for transverse sectioning. In addition, sections at 6 mm penetration, the critical regeneration distance observed in the experimental group, were further analyzed by (a) staining with hematoxylin and eosin (H&E), a common histological stain for visualizing cellular morphology, and (b) antibodies against neurofilament protein (NFP), a marker specific for neuronal axons.

Figure 5:
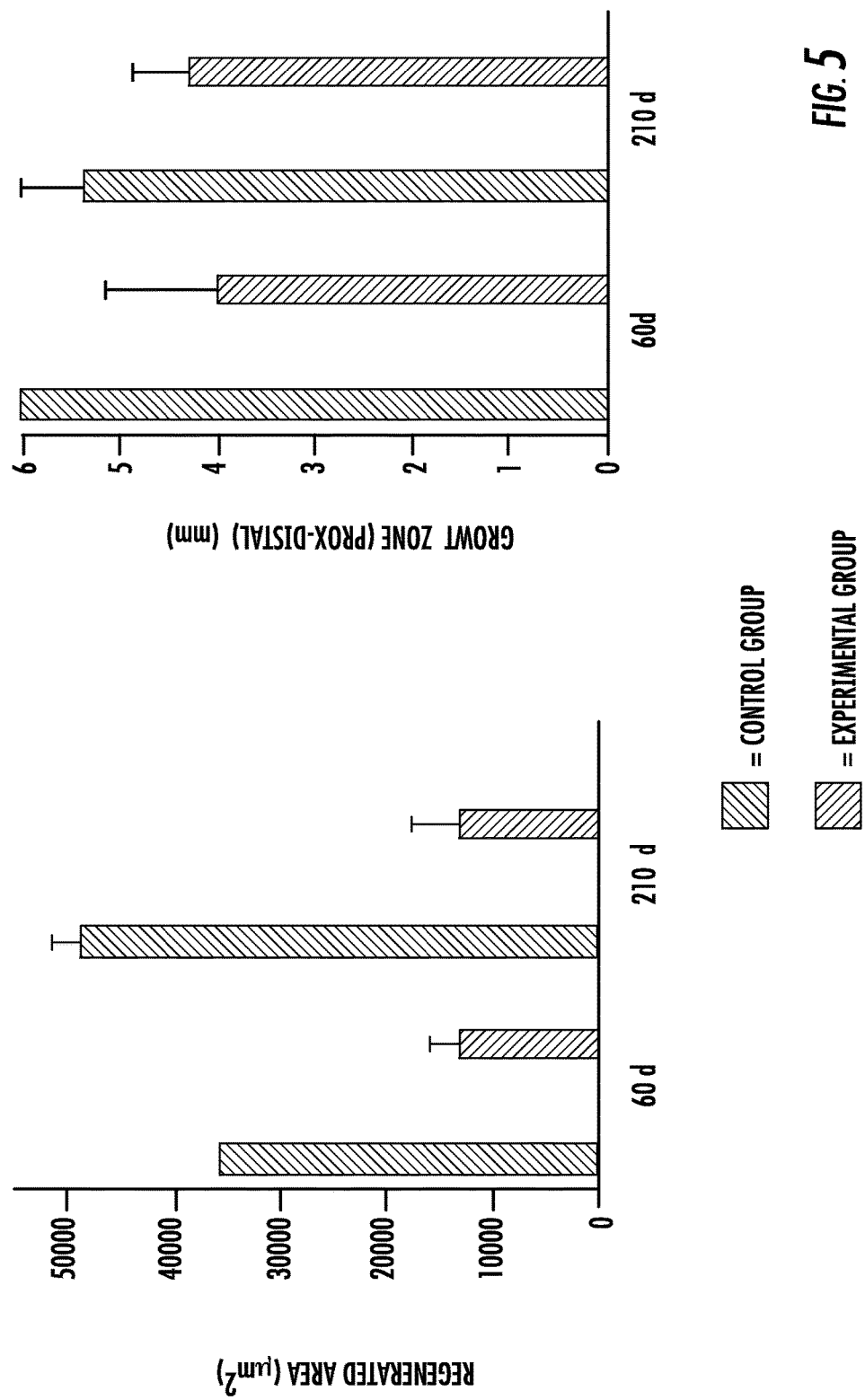
FIG. 5 illustrates a graph of some results of a method of inhibiting nerve growth according to one embodiment described herein.

Nerve growth and vascularization was observed in both the experimental and control groups after 210 days. Specifically, organized tissue regrowth consisting of axons, Schwann cells, and fibroblasts was observed within the microchannels of the tubes of each of the implants in both the control and experimental groups. Flat cells resembling a perineurium were organized around the outer layer of regenerating tissue, while NFP-positive axons were observed more centrally within the conduits. However, quantitative analysis of the regenerated nerve area indicated that nerve growth was statistically lower in the group treated with the experimental device. The number of regenerated axons in the experimental group was up to 50% less than in the control group. Moreover, the penetration of the regenerated nerves within the microchannels of the experimental device was limited to only the first 7 mm of the tube. In contrast, nerve cables reconnected to the distal nerve stump in each instance in the control group. Some results are illustrated in FIG. 5.

Figure 6:
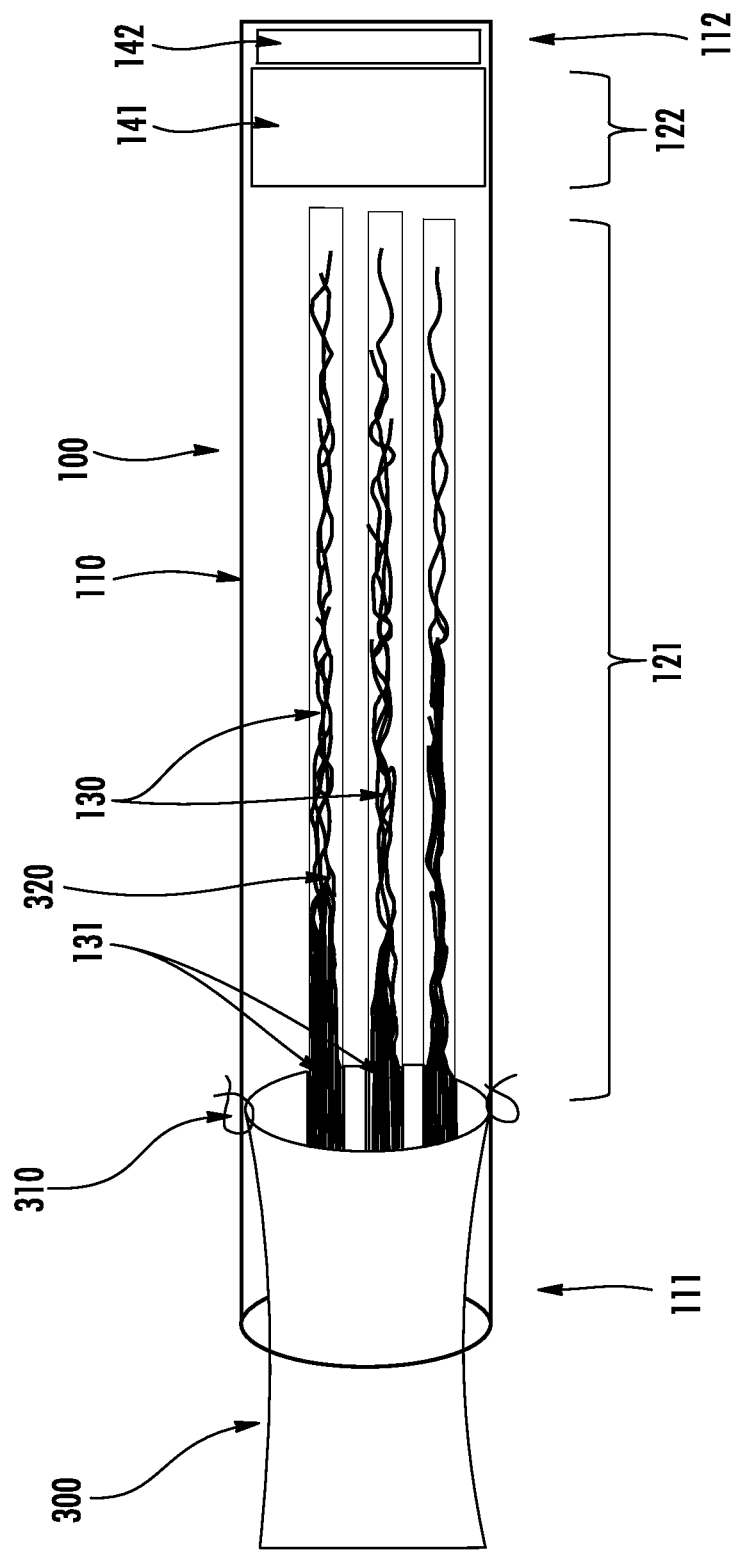
FIG. 6 illustrates a sectional view of a device used to inhibit nerve growth according to one embodiment described herein.

In addition, the growth of nerves within the experimental device is illustrated schematically in FIG. 6. As illustrated in FIG. 6, a nerve growth inhibition device (100) is disposed over a nerve stump (300). Specifically, the nerve stump is inserted into the tube (110) of the device (100) to a nerve insertion point (310) corresponding to the proximal end (131) of the microchannels (130). Regenerated nerve axons (320) initially are guided within the microchannels (130) toward the distal end (112) of the tube (110). Within a nerve growth region (121) of the device (100), the regenerated nerve axons (320) are viable. However, within a nerve growth inhibition region (122) of the device (100), growth of the nerve axons (320) is retarded and ultimately ceases.

EXAMPLE 4

Method of Providing Analgesia

A method of providing analgesia according to one embodiment described herein was carried out as follows. First, a device having a structure corresponding to Example 1 was used to reduce mechanically-induced pain caused by neuromas. Specifically, 17 adult Lewis rats were subjected to surgery according to the tibial neuroma transposition (TNT) model described in Dorsi et al., "The tibial neuroma transposition (TNT) model of neuroma pain and hyperalgesia," *Pain*, 134(3), 320-334 (2008). Briefly, the posterior tibial nerve of an anesthetized animal was exposed from approximately 8 mm proximal to the calcaneal branch to 1 mm distal to the plantar nerve bifurcation. The transected tibial nerve was then redirected to approximately 8-10 mm superior to the lateral malleolus in the hind limb in which the tibial nerve will be ligated and to the lateral side of the ankle. This transposition and superficial placement of the tibial nerve permitted routine screening for abnormal sensation at this site. Therefore, this model created a neuroma that was accessible for mechanical testing and allowed evaluation of pain perception in a way that resembles clinical evaluation of the Hoffman-Tinel sign in amputees (i.e., neuroma tenderness).

Mechanical testing was carried out using a von Frey test derived from a clinical procedure to assess allodynia, particularly in patients with neuropathic pain. The von Frey test is considered reliable to ascertain mechanoceptive pain in rats. The von Frey filaments were plastic hairs, 5 cm long and having various diameters, fixed on applicators. For testing, each animal was placed separately in a clear chamber with a wire-mesh floor and allowed to acclimate before testing. Each animal was then probed with a 300 g von Frey filament at the neuroma position. For comparison, the uninjured side was also palpated.

The animals were randomly assigned to three groups (each having n=4): (1) neuroma positive control, (2) treatment with a hollow non-biodegradable polyurethane tube, and (3) treatment with a device according to Example 1. Two months following the TNT surgery, all animals in groups (1) and (2) developed a vigorous paw withdrawal in response to von Frey stimulation at the ligature, which persisted for all three months over which these animals were observed. In sharp contrast, rats implanted with the nerve growth inhibition device of Example 1 showed a significant reduction in mechanically-induced pain.

Additionally, when the neuromas were dissected at the end of the study (after 8 months), conventional neuromas had formed in all control TNT animals. Those implanted with hollow polyurethane tubes showed no nerve growth into the nerve conduit, but clear neuromas formed at the proximal site. In contrast, the animals of group (3) showed no neuroma formation. Instead, nerve fiber growth into the device microchannels was observed. The regenerated fascicles extended inside the tube and then stopped at the middle of the tube's length. The binary composition of the matrix material hydrogel of the device promoted initial nerve growth into the microchannels (in regions comprising 1.5 wt. % agarose) but halted further growth when the nerves reached a higher density gel (3 wt. % agarose). The cyanoacrylate capping material added an extra level of safety, since it could prevent the escape of any nerve fibers that extended beyond the higher density gel. Thus, the regenerated nerves were essentially trapped inside the device.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A nerve growth inhibition device comprising:
  a tube having a proximal end and a distal end; and
  a matrix material disposed in the tube and comprising one or more microchannels, wherein the proximal end of the tube comprises an opening operable to receive nerve tissue, the distal end of the tube is sealed, the microchannels of the matrix material extend from the proximal end of the tube toward the distal end of the tube, and the sealed distal end of the tube blocks a distal end of the microchannels sufficiently to prevent nerve tissue disposed in the microchannels from exiting the microchannels on the distal end of the tube.

2. The device of claim 1, wherein the tube is sealed with a capping material disposed in the distal end of the tube and the capping material blocks or substantially blocks the distal end of the microchannels.

3. The device of claim 2, wherein the capping material comprises a gel, an adhesive, or a combination thereof.

4. The device of claim 2, wherein the capping material comprises agarose gel, a cyanoacrylate, or a combination thereof.

5. The device of claim 2, wherein the capping material comprises a plurality of capping layers.

6. The device of claim 5, wherein a first capping layer comprises agarose gel and a second capping layer comprises a cyanoacrylate.

7. The device of claim 1, wherein the matrix material comprises a plurality of microchannels.

8. The device of claim 1, wherein the matrix material comprises an agarose gel, a polylactic-co-glycolic acid, a polylactic acid, a caprolactone, or a combination thereof.

9. The device of claim 1, wherein the matrix material comprises an agarose gel.

10. The device of claim 1, wherein a fluid is disposed in the one or more microchannels.

11. The device of claim 10, wherein the fluid comprises a saline solution.

12. The device of claim 1, wherein the microchannels are free or substantially free of an extracellular matrix material disposed within the microchannels.

13. The device of claim 12, wherein the extracellular matrix material comprises collagen.

14. The device of claim 1, wherein the matrix material comprises a nerve growth region and a nerve growth inhibition region, and the nerve growth region is located nearer the proximal end of the tube compared to the nerve growth inhibition region.

15. The device of claim 14, wherein the nerve growth region allows the diffusion of growth signals and the nerve growth inhibition region blocks the diffusion of growth signals.

16. A method of inhibiting nerve growth comprising:
disposing a device in a biological compartment comprising nerve tissue, the device comprising
a tube having a proximal end and a distal end; and
a matrix material disposed in the tube and comprising one or more microchannels, wherein the proximal end of the tube comprises an opening operable to receive the nerve tissue, the distal end of the tube is sealed, the microchannels of the matrix material extend from the proximal end of the tube toward the distal end of the tube, and the sealed distal end of the tube blocks a distal end of the microchannels sufficiently to prevent the nerve tissue, when disposed in the microchannels, from exiting the microchannels on the distal end of the tube.

17. The method of claim 16, wherein the biological compartment comprises a stump of a severed nerve.

18. The method of claim 17, wherein the device is disposed over the nerve stump.

19. A method of providing analgesia comprising:
disposing a device in a biological compartment comprising nerve tissue, the device comprising
a tube having a proximal end and a distal end; and
a matrix material disposed in the tube and comprising one or more microchannels, wherein the proximal end of the tube comprises an opening operable to receive the nerve tissue, the distal end of the tube is sealed, the microchannels of the matrix material extend from the proximal end of the tube toward the distal end of the tube, and the sealed distal end of the tube blocks a distal end of the microchannels sufficiently to prevent the nerve tissue, when disposed in the microchannels, from exiting the microchannels on the distal end of the tube.

20. The method of claim 19, wherein the biological compartment comprises a stump of a severed nerve.

21. The method of claim 20, wherein the device is disposed over the nerve stump.

22. The device of claim 1, wherein the tube is sealed by a wall that is continuous with the remainder of the tube.

* * * * *